(12) United States Patent
Arita et al.

(10) Patent No.: US 7,847,131 B2
(45) Date of Patent: Dec. 7, 2010

(54) PROCESS FOR PRODUCING ACROLEIN

(75) Inventors: Yoshitaka Arita, Toride (JP); Tsukasa Takahashi, Himeji (JP); Masaki Okada, Toride (JP); Toshimitsu Moriguchi, Moriguchi (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 12/451,498

(22) PCT Filed: May 15, 2008

(86) PCT No.: PCT/JP2008/058948

§ 371 (c)(1),
(2), (4) Date: Nov. 16, 2009

(87) PCT Pub. No.: WO2008/140118

PCT Pub. Date: Nov. 20, 2008

(65) Prior Publication Data

US 2010/0113838 A1 May 6, 2010

(30) Foreign Application Priority Data

May 16, 2007 (JP) .............................. 2007-130938
Sep. 28, 2007 (JP) .............................. 2007-255727

(51) Int. Cl.
*C07C 45/52* (2006.01)

(52) U.S. Cl. ..................................... 568/486

(58) Field of Classification Search ................. 568/486; 502/208, 302
See application file for complete search history.

(56) References Cited

U.S. PATENT DOCUMENTS

| | | | |
|---|---|---|---|
| 1,916,743 A | 7/1933 | Schwenk et al. |
| 4,093,776 A | 6/1978 | Aoki et al. |
| 4,286,082 A | 8/1981 | Tsubakimoto et al. |
| 4,367,323 A | 1/1983 | Kitamura et al. |
| 4,446,261 A | 5/1984 | Yamasaki et al. |
| 4,625,001 A | 11/1986 | Tsubakimoto et al. |
| 4,683,274 A | 7/1987 | Nakamura et al. |
| 4,873,299 A | 10/1989 | Nowakowsky et al. |
| 4,973,632 A | 11/1990 | Nagasuna et al. |
| 4,985,518 A | 1/1991 | Alexander et al. |
| 5,124,416 A | 6/1992 | Haruna et al. |
| 5,145,906 A | 9/1992 | Chambers et al. |
| 5,244,735 A | 9/1993 | Kimura et al. |
| 5,250,640 A | 10/1993 | Irie et al. |
| 5,264,495 A | 11/1993 | Irie et al. |
| 5,380,808 A | 1/1995 | Sumiya et al. |
| 5,387,720 A | 2/1995 | Neher et al. |
| 5,426,249 A | 6/1995 | Haas et al. |
| 5,725,800 A * | 3/1998 | Huguenin ............. 252/301.4 P |
| 6,419,852 B1 * | 7/2002 | Braconnier et al. ... 252/301.4 P |
| 7,612,230 B2 | 11/2009 | Shima et al. |
| 2007/0129570 A1 | 6/2007 | Shima et al. |

FOREIGN PATENT DOCUMENTS

| | | |
|---|---|---|
| EP | 0 811 636 | 8/2001 |
| EP | 0 955 086 | 9/2003 |
| EP | 0 922 717 | 1/2005 |
| JP | 6-192147 | 7/1994 |
| JP | 6-211724 | 8/1994 |
| JP | 2005-213225 | 8/2005 |
| WO | 2007/119528 | 10/2007 |

* cited by examiner

*Primary Examiner*—Sikarl A Witherspoon
(74) *Attorney, Agent, or Firm*—Wenderoth, Lind & Ponack, L.L.P.

(57) ABSTRACT

There is provided a process for producing acrolein, which makes it possible to obtain acrolein in high yield by dehydration of glycerin. Glycerin is allowed to coexist with a catalyst containing a rare earth metal salt crystal of phosphoric acid, thereby dehydrating the glycerin, wherein the crystal is obtained by calcining a solid which is formed by allowing a liquid containing water and a hydroxide of the rare earth metal and/or a dehydration condensate of the hydroxide to contain phosphate ions.

7 Claims, No Drawings

PROCESS FOR PRODUCING ACROLEIN

FIELD OF THE INVENTION

The present invention relates to a process for producing acrolein by intramolecular dehydration of glycerin.

BACKGROUND ART

Biodiesel fuels have drawn much attention because they make low emission of carbon dioxide when used, and they can be used as alternate fuels for fossil fuels. Biodiesel fuels can be obtained by ester exchange reaction of vegetable oils, and it has been known that this reaction is accompanied by formation of glycerin as a by-product. Along with an increase in the demand and production of biodiesel fuels year by year, the formation of glycerin as a by-product has also been increased. In such a social climate, it has been required to make effective use of glycerin.

Acrolein is a compound obtained by intramolecular dehydration of glycerin and is useful as a raw material for acrolein derivatives such as 1,3-propanediol, methionine, acrylic acid, 3-methylthiopropionaldehyde, and water-absorbent resins. The production of acrolein from glycerin is to widen the application range of glycerin to the use as a raw material for acrolein derivatives. Therefore, it makes possible effective use of glycerin and also widens the application range of the by-product in the production of biodiesel fuels, thereby improving the economic value of the production of biodiesel fuels.

It has heretofore been known in the art that glycerin is used as a raw material for acrolein. For example, Japanese Patent Laid-open Publication (Kokai). No. Hei 6-192147 discloses that acrolein is obtained by dehydration of glycerin in the process of obtaining 1,2-propanediol and 1,3-propanediol from glycerin. Japanese Patent Laid-open Publication (Kokai) No. 2005-213225 discloses that acrolein is obtained by gas-phase dehydration of glycerin in the process of obtaining acrylic acid from glycerin.

Acrolein is usually produced using a catalyst for promoting intramolecular dehydration of glycerin. International Publication WO2007/119528 corresponding to the International Patent Application by the present applicant discloses that yttrium salt crystals, lanthanum salt crystals, cerium salt crystals, or samarium salt crystals of phosphoric acid are used as a catalyst. In the process for producing acrolein using these salt crystals, when glycerin gas is employed as a raw material, the deposition of carbonaceous substance on the surface of a catalyst, which is one of the factors for the deactivation of the catalyst, is suppressed. Similarly to how the suppression of such a deposition is being desired in the production of acrolein, a process for producing acrolein in high yield is also inevitably desired.

DISCLOSURE OF THE INVENTION

Under the above circumstances, it is an object of the present invention to provide a process for producing acrolein, which makes it possible to obtain acrolein in high yield by dehydration of glycerin.

The present inventors have intensively studied to obtain acrolein in high yield, and as a result, they have found that when rare earth meal salt crystals of phosphoric acid are used as a catalyst, the yield of acrolein can be improved, if the rare earth metal salt crystals are produced by a specific method, thereby completing the present invention.

That is, the present invention provides a process for producing acrolein in the presence of a catalyst, wherein the catalyst comprises a rare earth metal salt crystal of phosphoric acid and the crystal is obtained by calcining a solid which is formed by allowing a liquid containing water and a hydroxide of the rare earth metal and/or a dehydration condensate of the hydroxide to contain phosphate ions. In the process for producing acrolein according to the present invention, a solid is formed in a liquid allowed to contain water, a hydroxide of a rare earth metal and/or a dehydration condensate of the hydroxide, and phosphate ions, followed by calcination, and glycerin is dehydrated using a catalyst containing a rare earth metal salt crystal of phosphoric acid, which is obtained by the calcination, thereby making it possible to obtain acrolein in high yield.

Both a process for dehydrating glycerin by gas-phase dehydration in which glycerin gas is brought into contact with a catalyst and a process for dehydrating glycerin by liquid-phase dehydration in which liquid glycerin is brought into contact with a catalyst correspond to the process for producing acrolein according to the present invention. In these processes, preferred is a process for dehydrating glycerin by gas-phase dehydration, which is excellent in the industrial productivity of acrolein.

The hydroxide of a rare earth metal and/or the dehydration condensate of the hydroxide may preferably be produced by mixing an alkaline compound in an aqueous solution of a water-soluble rare earth metal salt. The water-soluble rare earth metal salt may preferably be one kind or two or more kinds of salts selected from nitrates, carbonates, chlorides, and organic acid salts.

The rare earth metal in the crystal may preferably be one kind or two or more kinds of rare earth metals selected from Y, La, Ce, Pr, and Nd, and particularly preferred is Nd because it gives a particularly high yield of acrolein.

The catalyst of the present invention is used in the process for producing acrolein according to the present invention, wherein the catalyst comprises a rear earth metal salt crystal of phosphoric acid and the crystal is obtained by calcining a solid which is formed by allowing a liquid containing water and a hydroxide of the rare earth metal and/or a dehydration condensate of the hydroxide to contain phosphate ions.

The process for producing an acrolein derivative according to the present invention comprises the steps of using the process for producing acrolein according to the present invention. Examples of the acrolein derivative may include 1,3-propanediol, methionine, 3-methylpropionaldehyde, acrylic acid, and water-absorbent resins such as polyacrylic acid, polyacrylic acid salts, and sodium polyacrylate.

BEST MODE FOR CARRYING OUT THE INVENTION

The present invention will be explained by reference to an embodiment. The process for producing acrolein according to this embodiment comprises causing intramolecular dehydration of glycerin by allowing the glycerin to coexist with a catalyst.

If the catalyst contains a rare earth metal salt crystal of phosphoric acid as a catalytic active component, the catalyst is not particularly limited, so long as the catalyst contains the catalytic active component. That is, part or all of the catalyst may be a rare earth metal salt crystal of phosphoric acid, regardless of whether the crystal is one kind or two or more kinds of crystals.

The catalyst may have a carrier on which a rare earth metal salt crystal of phosphoric acid is supported. Examples of the carrier in this case may include inorganic oxides such as $SiO_2$, $Al_2O_3$, $TiO_2$, and $ZrO_2$, and composite oxides; crystalline metallosilicates such as zeolites; and metals such as stainless steels and aluminum.

The shape of the catalyst is not particularly limited and may be, for example, spherical, column-shape, ring-shape, saddle-shape, honeycomb, or sponge-shape.

A rare earth metal as a constituent atom of a rare earth metal salt crystal of phosphoric acid may be any of the cerium group (La, Ce, Pr, Nd, Pm, and Sm), yttrium group (Sc, Y, Eu, Gd, Tb, Dy, Ho, Er, Tm, Yb, and Lu), lanthanides (Ce, Pr, Nd, Pm, Sm, Eu, Gd, Tb, Dy, Ho, Er, Tm, Yb, and Lu), and lanthanum group (La, Ce, Pr, Nd, Pm, Sm, Eu, Gd, Tb, Dy, Ho, Er, Tm, Yb, and Lu). That is, the rare earth metal may be any of 17 kinds of rare earth metals. A particularly preferred rare earth metal is Nd.

The composition in the rare earth metal salt crystal of phosphoric acid is not particularly limited. The composition may be, for example, $MPO_4$ (M denotes a rare earth metal) such as $ScPO_4$, $YPO_4$, $LaPO_4$, $CePO_4$, $PrPO_4$, $NdPO_4$, $SmPO_4$, $EuPO_4$, $GdPO_4$, $TbPO_4$, $HoPO_4$, $ErPO_4$, $TmPO_4$, and $YbPO_4$.

When the mole number of rare earth metal atom and the mole number of phosphoric atom in the rare earth metal salt crystal of phosphoric acid are defined as [M] and [P], respectively, they may favorably meet $0.10 \leqq [M]/[P] \leqq 2.00$, preferably $0.50 \leqq [M]/[P] \leqq 1.50$, and more preferably $0.70 \leqq [M]/[P] \leqq 1.25$.

The structure of a rare earth metal salt crystal of phosphoric acid is not also particularly limited and may be tetragonal, monoclinic, hexagonal, or the like.

To obtain a rare earth metal salt crystal of phosphoric acid, a liquid containing water and a hydroxide of the rare earth metal and/or a dehydration condensate of the hydroxide (hereinafter referred to as the "precursor-containing liquid" in some cases) is prepared, and a solid formed by allowing this solution to contain phosphate ions is calcined. The reason has not been made clear, but if a catalyst containing a rare earth metal salt crystal of phosphoric acid obtained by such a production method is used, a higher yield of acrolein can be achieved in comparison with a case where a catalyst containing a crystal obtained by another production method (e.g., a co-precipitation method; a method of concentrating a mixed liquid of a rare earth metal ion and phosphoric acid, followed by drying and calcination) is used.

A hydroxide of a rare earth metal is a compound expressed as $M(OH)_2$, $M(OH)_3$, or $M(OH)_4$ wherein M denotes the rare earth metal. Further, a dehydration condensate of the hydroxide of the rare earth metal is obtained by dehydration condensation of two or more kinds of the above hydroxides and may be a dimer of the above hydroxide, which is defined as $(HO)_2M—O-M(OH)_2$, or a hexamer of the above hydroxide, which is defined below.

[Chemical Formula 1]

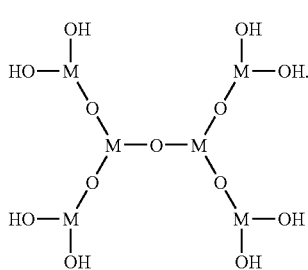

To prepare the precursor-containing liquid, a hydroxide of a rare earth metal and/or a dehydration condensate of the hydroxide may be dispersed in a water-containing solvent. Further, to prepare the precursor-containing liquid, there may also be mixed one kind or two or more kinds of salts selected from water-soluble rare earth metal salts, a water-containing solvent, and an alkaline compound. In this case, the mixing procedure may be, for example, (1) a method of mixing the solvent and the water-soluble rare earth metal salt and then adding the alkaline compound thereto or (2) a method of mixing the solvent and the alkaline compound and then adding the rare earth metal salt thereto, and the former method (1) may be preferred.

The solvent to be used for preparing the precursor-containing liquid is not particularly limited, if it contains water, and to produce a rare earth metal salt crystal of phosphoric acid at a low cost, it is favorable to use water alone as a solvent.

When the precursor-containing liquid is prepared by mixing a water-soluble rare earth metal salt in the solvent, the amount of rare earth metal salt is not particularly limited; however, the amount of rare earth metal salt may favorably be from 1% to 30% by mass, preferably from 2% to 20% by mass, and more preferably from 3% to 15% by mass, when the total amount of solvent and water-soluble rare earth metal salt is defined as 100% by mass.

A water-soluble rare earth meal salt may be either a rare earth metal salt of an organic acid or a rare earth metal salt of an inorganic acid, so long as it can be dissolved in the solvent, and there may be used one kind or two or more kinds of water-soluble rare earth metal salts. When a water-soluble rare earth metal salt is difficult to be dissolved in the solvent, the solvent may appropriately be heated or made to be acidic. Examples of the inorganic acid salt corresponding to the water-soluble rare earth metal salt may include nitrates such as $Sc(NO_3)_3$, $Y(NO_3)_2$, $Y(NO_3)_3$, $La(NO_3)_3$, $Ce(NO_3)_3$, $Ce(NO_3)_4$, $Pr(NO_3)_3$, $Nd(NO_3)_3$, $Sm(NO_3)_2$, $Sm(NO_3)_3$, $Eu(NO_3)_2$, $Eu(NO_3)_3$, $Gd(NO_3)_3$, $Tb(NO_3)_3$, $Ho(NO_3)_3$, $Er(NO_3)_3$, $Tm(NO_3)_3$, and $Yb(NO_3)_3$; carbonates such as $Sc_2(CO_3)_3$, $YCO_3$, $Y_2(CO_3)_3$, $La_2(CO_3)_3$, $Ce_2(CO_3)_3$, $Ce(CO_3)_2$, $Pr_2(CO_3)_3$, $Nd_2(CO_3)_3$, $SmCO_3$, $Sm_2(CO_3)_3$, $EuCO_3$, $Eu_2(CO_3)_3$, $Gd_2(CO_3)_3$, $Tb_2(CO_3)_3$, $Ho_2(CO_3)_3$, $Er_2(CO_3)_3$, $Tm_2(CO_3)_3$, and $Yb_2(CO_3)_3$; chlorides such as $ScCl_3$, $YCl_2$, $YCl_3$, $LaCl_3$, $CeCl_3$, $CeCl_4$, $NdCl_3$, $PrCl_3$, $SmCl_2$, $SmCl_3$, $EuCl_2$, $EuCl_3$, $GdCl_3$, $TbCl_3$, $HoCl_3$, $ErCl_3$, $TmCl_3$, $YbCl_3$, and $LuCl_3$; bromides such as $ScBr_3$, $YBr_2$, $YBr_3$, $LaBr_3$, $CeBr_3$, $CeBr_4$, $NdBr_3$, $PrBr_3$, $SmBr_2$, $SmBr_3$, $EuBr_2$, $EuBr_3$, $GdBr_3$, $TbBr_3$, $HoBr_3$, $ErBr_3$, $TmBr_3$, $YbBr_3$, and $LuBr_3$; iodides such as $ScI_3$, $YI_2$, $YI_3$, $LaI_3$, $CeI_3$, $CeI_4$, $NdI_3$, $PrI_3$, $SmI_2$, $SmI_3$, $EuI_2$, $EuI_3$, $GdI_3$, $TbI_3$, $HoI_3$, $ErI_3$, $TmI_3$, $YbI_3$, and $LuI_3$; $(NH_4)_2[Ce(NO_3)_6]$; and $(NH_4)_4[Ce (SO_4)_4]Ce (SO_4)_2$. Examples of the organic acid salt corresponding to the water-soluble rare earth metal salt may include formats such as $Sc(HCOO)_3$, $Y(HCOO)_2$, $Y(HCOO)_3$, $La(HCOO)_3$, $Pr(HCOO)_3$, and $Nd(HCOO)_3$; acetates such as $Sc(CH_3COO)_3$, $Y(CH_3COO)_2$, $Y(CH_3COO)_3$, $La(CH_3COO)_3$, $Ce(CH_3COO)_3$, $Ce(CH_3COO)_4$, $Pr(CH_3COO)_3$, $Nd(CH_3COO)_3$, $Sm(CH_3COO)_2$, $Sm(CH_3COO)_3$, $Eu(CH_3COO)_2$, $Eu(CH_3COO)_3$, $Gd(CH_3COO)_3$, $Tb(CH_3COO)_3$, $Dy(CH_3COO)_3$, $Ho(CH_3COO)_3$, $Er(CH_3COO)_3$, $Tm(CH_3COO)_3$, $Yb(CH_3COO)_3$, and $Lu(CH_3COO)_3$; oxalates such as $Sc_2(C_2O_4)_3$, $Y(C_2O_4)$, $Y_2(C_2O_4)_3$, $La_2(C_2O_4)_3$, $Ce_2(C_2O_4)_3$, $Ce(C_2O_4)_2$, $Pr_2(C_2O_4)_3$, $Sm(C_2O_4)$, $Sm_2(C_2O_4)_3$, $Eu(C_2O_4)$, $Eu_2(C_2O_4)_3$, $Tb_2(C_2O_4)_3$, $Dy_2(C_2O_4)_3$, $Ho_2(C_2O_4)_3$, $Er_2(C_2O_4)_3$, $Tm_2(C_2O_4)_3$, $Yb_2(C_2O_4)_3$, and $Lu_2(C_2O_4)_3$; and citrates such as $Y_3(C_6H_5O_7)_2$ and $Y (C_6H_5O_7)$. In the water-soluble rare earth metal salts exemplified above, preferred are nitrates.

The "alkaline compound" is a compound which makes the solvent alkaline when it is dissolved in the solvent of the precursor-containing liquid. Examples of the alkaline compound may include ammonia; aliphatic amines such as methyl amine, ethyl amine, n-propyl amine, isopropyl amine, sec-butyl amine, dimethyl amine, diethyl amine, trimethyl amine, and triethyl amine; alicyclic amines such as cyclohexyl amine; alkanol amines such as monoethanol amine, diethanol amine, and triethanol amine; pyridine; ammonium carbonate; and urea. Although a hydroxide of a rare earth metal may be produced by adding a hydroxide of an alkaline metal or the like, the compounds exemplified above may be preferred as the alkaline compound, because if the alkaline metal remains in the catalyst, it may adversely affect the catalyst performance, and particularly preferred is ammonia.

When the precursor-containing liquid is prepared by mixing an alkaline compound in the solvent, the amount of alkaline compound may favorably be an amount to make the pH of the solvent in the range of from 2 to 13, preferably an amount to make the pH of the solvent in the range of from 4 to 11, and more preferably an amount to make the pH of the solvent in the range of from 7 to 9. In the mixing of an alkaline compound, the alkaline compound may be mixed gradually at a constant rate or the alkaline compound may be mixed at once; however, to make uniform the particle size of a hydroxide of a rare earth metal salt and/or a dehydration condensate of the hydroxide, the former gradual mixing may be preferred. The temperature of an aqueous solution when mixing the alkaline compound is not particularly limited; however, taking into consideration the difficulty in pH adjustment due to the evaporation of a volatile alkaline compound when the volatile alkaline compound is selected as well as the reproducibility of the production of the hydroxide of the rare earth metal and/or the production of the dehydration condensate of the hydroxide, it may usually be from 1° C. to 50° C., preferably from 20° C. to 40° C. Further, after the completion of the mixing of the alkaline compound, it may be preferred not to add phosphoric acid immediately but to keep the resulting mixture still as it is. While the mixture is kept still, the particles of the hydroxide of the rare earth metal or the like are grown and the sizes of the particles become uniform.

To allow the precursor-containing liquid to contain phosphate ions, one kind or two or more kinds of compounds selected from phosphoric acids such as $H_3PO_4$, $H_4P_2O_7$, $H_5P_3O_{10}$, and $H_6P_4O_{10}$; phosphoric acid esters such as trimethyl phosphate and triethyl phosphate; ammonium phosphates such as ammonium dihydrogenphosphate and diammonium hydrogenphosphate; phosphorous oxides such as $P_4O_6$, $P_4O_8$, $P_4O_9$, and $P_4O_{10}$; and the like may be added to the precursor-containing liquid.

The addition rate when adding the above phosphoric acid, phosphoric acid ester, ammonium phosphate, phosphorous oxide, or the like, and the temperature at the addition (usually from 0° C. to 50° C.) are not particularly limited. Further, after the completion of the addition, it may be preferred to keep the resulting mixture still as it is. While the mixture is kept still, the amount of solid produced by allowing the precursor-containing liquid to contain phosphate ions is increased. A solid-containing product obtained by the production of the solid is a sol or gel.

If the above solid is calcined, the rare earth metal salt crystal of phosphoric acid can be obtained; however, a sol or gel of the solid-containing product contains a large amount of ammonium nitrate or the like, and if the solid-containing product is placed as it is in an atmosphere at the calcination temperature, a generated gas of ammonium nitrate or the like may possibly scatter or explode the rare earth metal salt crystal of phosphoric acid. To decrease a gas generated at the calcination, it may be preferred to place the solid-containing product in an atmosphere at a temperature lower than the calcination temperature. To decrease the gas, for example, the solid-containing product may be placed in an air atmosphere at from 150° C. to 230° C. or in an inert gas atmosphere at from 150° C. to 350° C. after water is removed from the solid-containing product.

In the calcination of a rare earth metal salt crystal of phosphoric acid, the crystallization of the metal salt tends to be promoted as the calcination temperature is higher and the crystallization of the metal salt tends to be promoted as the calcination time is longer. Taking those trends into consideration, the calcination temperature and the calcination time may appropriately be determined. The calcination conditions may favorably be in air at from 500° C. to 1,500° C. for from 3 to 15 hours, preferably at from 600° C. to 1,400° C. for from 3 to 10 hours, and more preferably at from 700° C. to 1,200° C. for from 3 to 5 hours.

A rare earth metal salt crystal of phosphoric acid, which is an active component of a catalyst, can be obtained by the above calcination. When the rare earth metal salt crystal of phosphoric acid is supported on a carrier, there can be utilized, for example, an ordinary catalyst preparation method such as an impregnation method, a deposition precipitation method, or a kneading method. The impregnation method may include (1) a mode of impregnating a carrier with the precursor-containing liquid and then allowing the impregnated precursor-containing liquid to contain phosphate ions, followed by calcination, and (2) a mode of impregnating a carrier with a phosphate ion-containing liquid and then impregnating the carrier with the precursor-containing liquid, followed by calcination. The deposition precipitation method involves producing a hydroxide of a rare earth metal and/or a dehydration condensate of the hydroxide in a dispersion of a carrier and then allowing the resulting precursor-containing liquid to contain phosphate ions, followed by calcination. The kneading method involves mixing a carrier with a solid produced by allowing the precursor-containing liquid to contain phosphate ions, followed by drying and calcination. In the kneading method, the carrier may be mixed with a sol or gel containing the solid and the carrier may also be mixed with a solid separated from the sol or gel.

Glycerin to be a raw material for the production of acrolein is not particularly limited and may be either purified glycerin or crude glycerin. The glycerin may also be glycerin derived from natural resources, for example, glycerin produced by ester exchange reaction of a vegetable oil such as palm oil, palm kernel oil, coconut oil, soybean oil, rape seed oil, olive oil, or sesame oil; or glycerin produced by ester exchange reaction of an animal fat or oil such as fish oil, beef tallow, lard, or whale oil. There may also be used glycerin chemically synthesized from ethylene, propylene, or the like.

The process for producing acrolein according to the present invention may utilize either of gas-phase dehydration by bringing glycerin gas into contact with a catalyst or liquid-phase dehydration by bringing liquid glycerin into contact with a catalyst. The following will describe, as an example, a process for producing acrolein, which utilizes gas-phase dehydration excellent in the industrial productivity of acrolein.

In the gas-phase dehydration of glycerin, a glycerin-containing gas is brought into contact with a catalyst in a reactor arbitrarily selected from fixed bed reactors, moving bed reactors, fluid bed reactors, and the like.

The concentration of glycerin in the glycerin-containing gas is not particularly limited; however, when it is necessary to adjust the concentration of glycerin in the glycerin-containing gas, one kind or two or more kinds of gases selected from condensable gases and noncondensable gases, both of which do not cause any adverse effect on the dehydration of glycerin to produce acrolein, may be added as a dilution gas to the glycerin-containing gas to adjust the glycerin concentration. To prepare the glycerin-containing gas containing a dilution gas, there may be carried out gasification of a solution containing glycerin and the dilution gas component or mixing of glycerin gas and the dilution gas.

To improve the selectivity and yield of acrolein in the gas-phase dehydration of glycerin and to decrease the amount of carbonaceous substance deposited to the surface of a catalyst to thereby improve the life of the catalyst, the partial pressure of glycerin gas may be adjusted to be low in the glycerin-containing gas. To improve the yield and the like, the partial pressure of glycerin gas may favorably be 30 kPa or lower, preferably 25 kPa or lower, more preferably 20 kPa or lower, and still more preferably 15 kPa or lower. Taking into consideration only an improvement in the yield of acrolein and the life of a catalyst, the partial pressure of glycerin may be favorable to be as low as possible; however, when the pressure (total pressure) of a glycerin-containing gas is lowered to realize the partial pressure, it requires a reactor provided with high air-tightness and resistance to pressure reduction and a large-scale decompressor. Further, when a great amount of dilution gas is used to lower the partial pressure, there are some problems to be considered, that is, it requires a large-scale reactor and a great amount of catalyst to make proper the contact time of the glycerin gas with the catalyst; the collection and purification of acrolein become difficult because the acrolein concentration becomes too low in the gas after the dehydration of glycerin; and the acrolein concentration cannot be proper in some cases as a raw material for the production of an acrolein derivative such as acrylic acid unless the acrolein in the gas is concentrated after the dehydration of glycerin. Taking these facts into consideration, the partial pressure of glycerin gas may favorably be 0.01 kPa or higher, preferably 1.0 kPa or higher, and more preferably 2.0 kPa or higher. The partial pressure of glycerin gas is a pressure at the inlet of a reactor, and when a dilution gas is contained in the glycerin-containing gas, the partial pressure of glycerin gas is a value calculated from the pressure (total pressure) of the glycerin-containing gas at the inlet of a reactor and the molar concentration (mol %) of glycerin.

Acrolein is produced without arbitrarily setting the pressure of a glycerin-containing gas. It is usual that the pressure may appropriately be set on the basis of a balance between the air-tightness and pressure resistance of a reactor and the performance of a catalyst, and the pressure of a glycerin-containing gas may favorably be from 0.01 kPa to 1 MPa, preferably from 0.1 kPa to 500 kPa, more preferably from 1 kPa to 300 kPa, and still more preferably from 1 kPa to 200 kPa.

When the concentration of glycerin in the glycerin-containing gas is adjusted using a dilution gas, a condensable gas to be used as the dilution gas is a gas of a compound having a boiling point which is higher than that of acrolein and which is 200° C. or lower under the normal pressure condition. Examples of the condensable gas may include water vapor; gases of alkane compounds such as hexane, heptane, octane, and cyclohexane; and gases of aromatic compounds such as benzene, toluene, xylene, mesitylene, and ethylbenzene. When water vapor is selected, the life of a catalyst and the yield of acrolein can be improved. To suppress energy consumption when heating and/or cooling a glycerin-containing gas and at the same time to suppress the cost of separating acrolein from a condensable gas, the concentration of condensable gas in the glycerin-containing gas may favorably be 80 mol % or lower, preferably 40 mol % or lower, and more preferably 10 mol % or lower. The partial pressure of a condensable gas may preferably be not higher than 5 times, more preferably not higher than 4 times, and still more preferably not higher than 1 time, as much as the partial pressure of glycerin gas, from the viewpoints of energy requirement for generating a condensable gas and compressing the condensable gas flowing out of a reactor as well as wastewater treatment.

A noncondensable gas to be used as the dilution gas of a glycerin-containing gas is a gas of a compound or a simple substance having a boiling point of 0° C. or lower under the normal pressure condition. Examples of the noncondensable gas may include nitrogen gas, carbon dioxide gas, oxygen-containing gases such as air, and rare gases such as helium. When oxygen is selected, the deposition amount of carbonaceous substance on the surface, of a catalyst can be lowered. Further, if it falls into the category of the noncondensable gas, an off-gas such as a gas discharged after the collection of acrolein from the gas after the dehydration of glycerin and a gas discharged in the production of an acrolein derivative such as acrylic acid can be recycled and used partially or entirely as a dilution gas. The concentration of noncondensable gas in the glycerin-containing gas may favorably be 40 mol % or lower. To suppress energy consumption when heating and/or cooling the glycerin-containing gas and at the same time to decrease the scattering loss of acrolein when liquefying and recovering the acrolein, the concentration of noncondensable gas in the glycerin-containing gas may favorably be 10 mol % or lower, preferably 8 mol % or lower, and more preferably 5 mol % or lower. Further, the partial pressure of a noncondensable gas may favorably be not higher than 2 times, preferably not higher than 1 time, and more preferably not higher than 0.5 times, as much as the partial pressure of glycerin gas. In addition, when oxygen is used as a dilution gas, the amount of oxygen in the glycerin-containing gas may preferably be 20 mol % or lower (preferably 15 mol % or lower), or not higher than 3.5 times as much as the partial pressure of glycerin gas, whichever is the lower value, to avoid a decrease in the yield of acrolein due to combustion reaction.

In terms of the flow rate (flow rate: GHSV) of the glycerin-containing gas per unit catalyst volume, the flow rate of the glycerin-containing gas to a reactor may usually be from 10 to 30,000 $hr^{-1}$, favorably from 30 to 20,000 $hr^{-1}$, preferably from 50 to 12,000 $hr^{-1}$, more preferably from 70 to 10,000 $hr^{-1}$, and still more preferably from 100 to 5,000 $hr^{-1}$. To produce acrolein economically at a high efficiency, it may favorably be 3,000 $hr^{-1}$ or lower. The GHSV of the glycerin-containing gas is determined on the basis of the flow rate itself of the glycerin-containing gas at the inlet of a reactor and is different from the GHSV of the glycerin gas described below in terms of the determination method (when glycerin in the glycerin-containing gas is 100 mol %, the GHSV of the glycerin gas described below is employed).

The GHSV of glycerin gas is a value calculated according to the equation: (mass ratio of glycerin in glycerin-containing gas)×(mass of glycerin-containing gas per 1 L of catalyst and 1 hour)×(volume of 1 molar ideal gas under normal condition)/(molecular weight of glycerin). For example, when a glycerin-containing gas having a glycerin content of 90% by mass is fed at a flow rate of 1,000 $g \cdot hr^{-1}$ to a reactor filled with 1 L of a catalyst, the GHSV of glycerin gas is 0.9×1,000 $g \cdot hr^{-1}$×22.4 L÷92.06 g=219 $hr^{-1}$. The GHSV of glycerin gas may usually be from 70 to 3,650 $hr^{-1}$, favorably from 80 to 2,400 $hr^{-1}$, preferably from 100 to 1,200 $hr^{-1}$, more preferably from 125 to 1,200 $hr^{-1}$, and still more preferably from 125 to 600 $hr^{-1}$, taking into consideration industrial viewpoints such as economic efficiency, e.g., downsizing of a reactor, the life of a catalyst, and the production efficiency of acrolein.

In the gas-phase dehydration reaction of glycerin, if the reaction temperature is too lower or too higher, the yield of acrolein is lowered; therefore, the reaction temperature may favorably be from 200° C. to 500° C., preferably from 250° C. to 450° C., more preferably from 300° C. to 450° C., and still more preferably from 350° C. to 400° C. The "reaction temperature" in the gas-phase dehydration reaction as used herein means the preset temperature of a heat medium or the like to carry out the temperature control of a reactor.

To recover acrolein gas flowing out of a reactor, there may favorably be used a method of condensing the acrolein gas or a method of allowing the acrolein gas to be absorbed into an acrolein-dissolving solvent such as water. When a dilution gas is discharged in this recovery, part or all of the discharged dilution gas may be reused as a dilution gas for the glycerin-containing gas to be fed into a reactor.

Acrolein can be produced by the process as described above. When the gas-phase dehydration is continued, the activity of a catalyst is consequently lowered to a level insufficient for the industrial production of acrolein; however, if the catalyst is regenerated, the activity of the catalyst can be increased to a level suitable for practical use.

If a gas for regeneration is brought into contact with a catalyst at a high temperature, carbonaceous substance deposited to the surface of the catalyst can be removed to regenerate the catalyst. The "gas for regeneration" is a gas containing an oxidizing gas. Example of the oxidizing gas may include oxygen and air containing oxygen. Further, a gas inert to the catalyst regeneration reaction, such as nitrogen, carbon dioxide, and water vapor, may be added to a gas for regeneration. When there is concern that rapid heat generation may occur by contact of oxygen with a catalyst, the addition of an inert gas to a gas for regeneration is recommended also for the purpose of suppressing the rapid heat generation.

A method of bringing a catalyst into contact with a gas for regeneration is not particularly limited, but may be, for example, a method of bringing a catalyst taken out a reactor into contact with a gas for regeneration or a method of allowing a gas for regeneration to pass through a reactor after the dehydration of glycerin. The latter method of allowing a gas for regeneration to pass through a reactor may be preferred because there is no need to remove a catalyst from the reactor and to fill again the reactor with the catalyst.

The temperature at the contact with the above gas for regeneration may appropriately be set to be a temperature suitable for removing carbonaceous substance. For example, when a gas for regeneration is allowed to pass through a reactor, the temperature of a heat medium or the like for carrying out the temperature control of the reactor may favorably be set to 330° C. or higher, preferably 350° C. or higher, and the upper limit of the temperature is a temperature suitable for avoiding thermal deterioration of the catalyst.

As already known in the art, acrolein thus produced can be used as a raw material for producing an acrolein derivative such as acrylic acid, 1,3-propanediol, allyl alcohol, polyacrylic acid, and polyacrylic acid salts. Accordingly, the above process for producing acrolein can inevitably be incorporated in the process for producing an acrolein derivative.

For example, acrylic acid can be produced by oxidation of acrolein.

Before oxidation of acrolein, it may be preferred to decrease the amount of 1-hydroxyacetone and phenol to be incorporated in the oxidation system from the viewpoint of improving the yield of acrylic acid. In the process for producing acrolein according to the present embodiment, 1-hydroxyacetone and/or phenol may be produced as by-products in some cases.

Phenol and 1-hydroxyacetone are compounds which may cause a decrease in the yield of acrylic acid; therefore, the amounts of both compounds removed may favorably be as much as possible. When the amount of phenol after the removal is defined as a ratio (Ph/A) of the mass of phenol (Ph) to the mass of acrolein (A), Ph/A may favorably be 0.020 or lower, preferably 0.010 or lower, and more preferably 0.005 or lower. Further, when the amount of 1-hydroxyacetone after removal is defined as a ratio (H/A) of the mass of 1-hydroxyacetone (H) to the mass of acrolein (A), H/A may favorably be 0.020 or lower, preferably 0.010 or lower, and more preferably 0.005 or lower.

By utilizing a difference in the boiling points among acrolein (boiling point: 53° C.), phenol (boiling point: 182° C.), and 1-hydroxyacetone (boiling point: 146° C.), phenol and/or 1-hydroxyacetone can be removed from acrolein. For such a removal, there may favorably be employed, for example, a method of distilling acrolein having a boiling point lower than those of substances to be removed by treating liquid acrolein in a distillation tower; a method of condensing substances to be removed which have boiling points higher than that of acrolein by treating gaseous acrolein in a condensation tower; and a method of evaporating acrolein having a boiling point lower than those of substances to be removed by blowing a gas into acrolein introduced into an evaporation tower. In addition, water or the like may be extracted with a solvent from acrolein before the removal of phenol and/or 1-hydroxyacetone.

To produce acrylic acid by oxidation of acrolein, it may be preferred to carry out gas-phase oxidation of acrolein at from 200° C. to 400° C. by the coexistence of a catalyst and an acrolein-containing gas in an oxidation reactor arbitrarily selected from fixed bed reactors, moving bed reactors, fluid bed reactors, and the like.

The catalyst to be used in the above oxidation is not particularly limited, so long as it may be a catalyst to be used for the case where acrylic acid is produced by a catalytic gas-phase oxidation method using acrolein or an acrolein-containing gas together with molecular state oxygen or a gas containing molecular state oxygen. Examples of the catalyst may include mixtures of metal oxides such as iron oxide, molybdenum oxide, titanium oxide, vanadium oxide, tungsten oxide, antimony oxide, tin oxide, and copper oxide; and composites of these metal oxides. In these catalysts exemplified above, molybdenum-vanadium type catalysts containing molybdenum and vanadium as main constituent metals may be preferred. Further, the catalyst may be those in which the above mixtures and/or composites are supported on a carrier (e.g., zirconia, silica, alumina, and their composites, as well as silicon carbide).

With respect to the amount of oxygen to be added to a gas of the acrolein-containing composition to be used in the production of acrylic acid, there is a possibility that combustion may be caused while being accompanied with a risk of explosion when the amount of oxygen to be added is excess, and therefore, it follows that the upper limit thereof should appropriately be set.

To recover the acrylic acid gas produced by the gas-phase oxidation, an absorption tower may be used, which makes it possible to cool acrylic acid or allow acrylic acid to be absorbed in a solvent such as water.

It has been known in the art that acrylic acid thus produced can be used as a raw material for an acrylic acid derivative such as acrylic acid esters and polyacrylic acid, and therefore, the above process for producing acrylic acid can be used as a step of producing acrylic acid in the process for producing an acrylic acid derivative.

When polyacrylic acid is produced using the acrylic acid obtained, polyacrylic acid capable of being used as a water-absorbent resin can be produced using the aqueous solution polymerization method or the reverse-phase suspension polymerization method. The aqueous solution polymerization method is a method in which acrylic acid in an aqueous solution of acrylic acid is polymerized without using any dispersion solvent, and is disclosed in U.S. Pat. Nos. 4,625,001, 4,873,299, 4,286,082, 4,973,632, 4,985,518, 5,124,416, 5,250,640, 5,264,495, 5,145,906, and 5,380,808, and European Patent Publications Nos. 0 811 636, 0 955 086, and 0 922 717. The reverse-phase suspension polymerization method is a polymerization method in which an aqueous solution of acrylic acid as a monomer is suspended in a hydrophobic organic solvent, and is disclosed in U.S. Pat. Nos. 4,093,776, 4,367,323, 4,446,261, 4,683,274, and 5,244,735.

EXAMPLES

The present invention will be explained below more specifically by reference to Examples, but the present invention is not limited to the following Examples. The present invention can be put into practice after appropriate modifications or variations within a range meeting the gists described above and later, all of which are included in the technical scope of the present invention.

The details about the methods of analysis for catalyst composition and crystal structure, the method of measurement for the amount of carbonaceous substance on the surface of catalysts, the method of catalyst preparation, and the production of acrolein are as follows.

(X-Ray Fluorescence (XRF) Analysis)

Using the Philips "PW2404" X-ray fluorescence spectrometer, rare earth metal atom (M atom) and phosphorus atom in catalysts were analyzed by the glass bead method. The quantitative analysis of M atom and phosphorus atom was carried out using a calibration curve produced with previously prepared standard samples.

(X-Ray Diffraction (XRD) Analysis)

Using the Rigaku "RINT-TTR III" Powder X-Ray diffractometer, the crystal structures of catalysts were analyzed under the following conditions.

X-ray source: Cu
Filter: not used
X-ray tube voltage: 50 kV
X-ray tube current: 300 mA
Divergence slit: 1/3°
Scattering slit: 1/2°
Receiving slit: open
Scanning range: from 5° to 90°
Sampling width: 0.02°
Scanning rate: 3.000°/sec (Measurement for Amount of Carbonaceous Substance)

Using a thermogravimetry-differential thermal analyzer (TG-DTA), each catalyst was placed under an air flow and then heated from room temperature to 900° C. at a rate of 10° C./min, and the mass change of the catalyst was measured as the amount of carbonaceous substance deposited to the catalyst in the production of acrolein.

(Preparation of Catalysts)

Catalysts were prepared by the following sol-gel method or co-precipitation method. The types of water-soluble rare earth metal salts to be used in the preparation of catalysts; the amounts of water-soluble rare earth metal salts, phosphoric acid, and ammonia water to be used; the calcining temperature in the preparation of catalysts were shown in Table 1 below. The P/M (P: mole number of phosphorus atom, M: mole number of rare earth metal atom) calculated from the results of XRF analysis for catalysts prepared; and the catalyst compositions and crystal structures as the results of XRD analysis were also shown in Table 1 below.

Preparation of Catalysts by Sol-Gel Method:

To a 10 wt % water-soluble rare earth metal salt aqueous solution at 30° C. under stirring, 28 wt % ammonia water was added dropwise at a constant rate over 3 hours using a pump for high-performance liquid chromatography ("L7110" available from Hitachi, Ltd.). The solution after the dropwise addition was aged by being left for 15 hours under stirring to obtain a precursor-containing liquid (i.e., a liquid containing a hydroxide of the rare earth metal and a dehydration condensate of the hydroxide). In the precursor-containing liquid under stirring, an 85 wt % $H_3PO_4$ aqueous solution was added dropwise at a constant rate over 3 hours using a pump for high-performance liquid chromatography, so that the precursor-containing liquid was allowed to contain phosphate ions. Thereafter, the precursor-containing liquid was left for 15 hours under stirring to obtain a sol or gel. The sol or gel was dehydrated under the conditions of 0.005 MPa and 60° C., followed by drying in an air atmosphere under the conditions of 120° C. and 10 hours. Then, the dried product was placed in a nitrogen atmosphere at 300° C. for 10 hours to separate ammonium nitrate from the dried product. Thereafter, the dried product was calcined in air over 5 hours to obtain rare earth metal salt crystals of phosphoric acid. The crystals were pulverized and classified with sieves each having a mesh of from 0.75 to 2.00 mm to obtain a catalyst.

Preparation of Catalysts by Co-Precipitation Method:

A 10 wt % water-soluble rare earth metal salt and an 85 wt % phosphoric acid aqueous solution were mixed to prepare a transparent mixed solution at 30° C. To this mixed solution under stirring, 28 wt % ammonia water was added dropwise at a constant rate over 3 hours using a pump for high-performance liquid chromatography (precipitates were produced from the beginning of the dropwise addition). The solution after the dropwise addition was aged by being left for 15 hours under stirring, and the precipitates thus produced were separated by filtration and dried in an air atmosphere under the conditions of 120° C. and 10 hours. Then, the dried product was placed in a nitrogen atmosphere at 300° C. for 10 hours to separate ammonium nitrate from the dried product. Thereafter, the dried product was calcined in air for 5 hours to obtain rare earth metal salt crystals of phosphoric acid. The crystals were pulverized and classified with sieves each having a mesh of from 0.75 to 2.00 mm to obtain a catalyst.

TABLE 1

| | | Preparation method of catalysts | | | | | | | |
|---|---|---|---|---|---|---|---|---|---|
| | | Amounts to be used (g) | | | | | | Catalysts | |
| | Preparation method | Water-soluble rare earth metal salt | | Phosphoric acid aqueous solution | Ammonia water | P/M (mol/mol) | Calcination temperature (° C.) | P/M (mol/mol) | Catalyst composition | Crystal structure |
| Ex. 1a | Sol-gel method | $Y(NO_3)_3 \cdot 6H_2O$ | 208.5 | 62.7 | 132.3 | 1 | 600 | 1.05 | $YPO_4$ $YPO_4$ | tetragonal Xenotime tetragonal |
| Ex. 1b | Sol-gel method | $Y(NO_3)_3 \cdot 6H_2O$ | 208.5 | 62.7 | 132.3 | 1 | 1,100 | 1.07 | $YPO_4$ | Xenotime tetragonal |
| Ex. 2a | Sol-gel method | $La(NO_3)_3 \cdot 6H_2O$ | 194.9 | 49.3 | 104.0 | 1 | 600 | 1.04 | $LaPO_4$ | Monazite monoclinic |

TABLE 1-continued

Preparation method of catalysts

| | | Amounts to be used (g) | | | | Calcination | | Catalysts | |
|---|---|---|---|---|---|---|---|---|---|
| | Preparation method | Water-soluble rare earth metal salt | | Phosphoric acid aqueous solution | Ammonia water | P/M (mol/mol) | temperature (° C.) | P/M (mol/mol) | Catalyst composition | Crystal structure |
| Ex. 2b | Sol-gel method | La(NO$_3$)$_3$•6H$_2$O | 194.9 | 49.3 | 104.0 | 1 | 800 | 0.99 | LaPO$_4$ | Monazite monoclinic |
| Ex. 3a | Sol-gel method | Ce(NO$_3$)$_3$•6H$_2$O | 188.5 | 49.0 | 103.6 | 1 | 600 | 0.95 | CePO$_4$ | Monazite monoclinic |
| Ex. 3b | Sol-gel method | Ce(NO$_3$)$_3$•6H$_2$O | 188.5 | 49.0 | 103.6 | 1 | 1,000 | 0.95 | CePO$_4$ | Monazite monoclinic |
| Ex. 4a | Sol-gel method | Pr(NO$_3$)$_3$•6H$_2$O | 184.6 | 48.9 | 103.1 | 1 | 600 | 1.10 | PrPO$_4$ | Monazite monoclinic |
| Ex. 4b | Sol-gel method | Pr(NO$_3$)$_3$•6H$_2$O | 184.6 | 48.9 | 103.1 | 1 | 800 | 1.11 | PrPO$_4$ | Monazite monoclinic |
| Ex. 5a | Sol-gel method | Nd(NO$_3$)$_3$•6H$_2$O | 183.4 | 48.2 | 101.7 | 1 | 600 | 1.16 | NdPO$_4$ | Monazite monoclinic |
| Ex. 5b | Sol-gel method | Nd(NO$_3$)$_3$•6H$_2$O | 183.4 | 48.2 | 101.7 | 1 | 1,000 | 1.12 | NdPO$_4$ | Monazite monoclinic |
| Comp. Ex. 1 | Coprecipitation method | Y(NO$_3$)$_3$•6H$_2$O | 208.5 | 62.7 | 12.3 | 1 | 1,100 | 1.02 | YPO$_4$ | Xenotime tetragonal |
| Comp. Ex. 2a | Coprecipitation method | La(NO$_3$)$_3$•6H$_2$O | 194.9 | 49.3 | 104.0 | 1 | 900 | 0.83 | LaPO$_4$ | Monazite monoclinic |
| Comp. Ex. 2b | Coprecipitation method | La(NO$_3$)$_3$•6H$_2$O | 194.9 | 49.3 | 104.0 | 1 | 1,100 | 0.83 | LaPO$_4$ | Monazite monoclinic |
| Comp. Ex. 3a | Coprecipitation method | Ce(NO$_3$)$_3$•6H$_2$O | 188.5 | 49.0 | 103.6 | 1 | 600 | 1.07 | CePO$_4$ | Rabdophane hexagonal |
| Comp. Ex. 3b | Coprecipitation method | Ce(NO$_3$)$_3$•6H$_2$O | 188.5 | 49.0 | 103.6 | 1 | 1,100 | 0.96 | CePO$_4$ | Monazite monoclinic |
| Comp. Ex. 3c | Coprecipitation method | Ce(NO$_3$)$_3$•6H$_2$O | 188.5 | 49.0 | 103.6 | 1 | 1,200 | 0.94 | CePO$_4$ | Monazite monoclinic |

P/M: (mole number of phosphorous atom)/(mole number of rare earth metal atom)
Y(NO$_3$)$_3$•6H$_2$O: available from Kishida Chemical Co., Ltd.;
La(NO$_3$)$_3$•6H$_2$O: available from Wako Pure Chemical Industries, Ltd.;
Ce(NO$_3$)$_3$•6H$_2$O: available from Wako Pure Chemical Industries, Ltd.;
Pr(NO$_3$)$_3$•6H$_2$O: available from Mitsuwa Chemicals Co., Ltd.;
Nd(NO$_3$)$_3$•6H$_2$O: available from Mitsuwa Chemicals Co., Ltd.;
phosphoric acid aqueous solution: "85 wt % H$_3$PO$_4$ aqueous solution" available from Kishida Chemical Co., Ltd.;
ammonia water: "28 wt % aqueous ammonia solution" available from Wako Pure Chemical Industries, Ltd.

(Production of Acrolein)

A stainless steel reaction tube (inner diameter: 10 mm; and length: 500 mm) filled with 15 mL of a catalyst was prepared as a fixed bed reactor, and the reactor was immersed in a molten salt bath at 360° C. Thereafter, nitrogen gas was allowed to flow in the reactor at a rate of 62 mL/min for 30 minutes, and an 80 wt % glycerin-containing gas (glycerin-containing gas composition: 27 mol % glycerin, 34 mol % water, and 39 mol % nitrogen) was allowed to flow in the reactor at a rate (GHSV) of 640 hr$^{-1}$. For 30 minutes before a prescribed duration passed from the flowing of the glycerin-containing gas in the reactor, the gas flowing out the reactor was allowed to be absorbed in water, and the quantitative analysis of glycerin and acrolein in the water was carried out. In the analysis carried out herein, a gas chromatography (GC) system equipped with FID as a detector was used and an internal reference method was employed.

In the measurement for the amount of carbonaceous substance on the surface of catalysts using TG-DTA, each of the catalysts after 7 hours passed from the starting of the flowing of the glycerin-containing gas was used as a sample.

The conversion rate of glycerin (GLY conversion rate) was calculated on the basis of equation (1) below and the amount of carbonaceous substance deposited to the surface of a catalyst was calculated on the basis of equation (2) below. The selectivities of acrolein (ACR), propionaldehyde (PALD), 1-hydroxyacetone (HDAC), and phenol (PhOH) were calculated on the basis of equation (3) below. The yield of acrolein (ACR yield) was calculated on the basis of equation (4) below.

[Equation 1]

$$\text{GLY conversion rate (\%)} = (1 - \text{mole number of glycerin in flowing gas/mole number of glycerin allowed to flow in reactor for 30 minutes}) \times 100 \quad \text{Equation (1)}$$

[Equation 2]

$$\text{Deposition amount of carbonaceous substance} = (\text{TG–mass loss in DTA measurement})/(\text{TG–catalyst mass after DTA measurement}) \quad \text{Equation (2)}$$

[Equation 3]

$$\text{Selectivity (\%)} = (\text{total carbon mole number of any one kind of compound produced/total carbon mole number of all compounds produced}) \times 100 \quad \text{Equation (3)}$$

[Equation 4]

$$\text{ACR yield (\%)} = \text{GLY conversion rate} \times \text{Selectivity}/100 \quad \text{Equation (4)}$$

The conversion rate of glycerin (GLY conversion rate) and the deposition amount of carbonaceous substance on the surface of a catalyst are shown in Table 2 below.

TABLE 2

| | Catalysts | | | Calcination temperature (°C.) | GLY conversion rates (%) | | | Deposition amount (g) |
|---|---|---|---|---|---|---|---|---|
| | Preparation method | Catalyst composition | Crystal structure | | After 3 hours | After 5 hours | After 7 hours | |
| Ex. 1a | Sol-gel method | YPO₄ YPO₄ | tetragonal Xenotime tetragonal | 600 | 100.0 | 100.0 | 100.0 | 0.15 |
| Ex. 1b | Sol-gel method | YPO₄ | Xenotime tetragonal | 1,100 | 100.0 | 100.0 | 100.0 | 0.067 |
| Ex. 2a | Sol-gel method | LaPO₄ | Monazite monoclinic | 600 | 100.0 | 100.0 | 100.0 | 0.32 |
| Ex. 2b | Sol-gel method | LaPO₄ | Monazite monoclinic | 800 | 100.0 | 100.0 | 100.0 | 0.23 |
| Ex. 3a | Sol-gel method | CePO₄ | Monazite monoclinic | 600 | 100.0 | 100.0 | 100.0 | 0.27 |
| Ex. 3b | Sol-gel method | CePO₄ | Monazite monoclinic | 1,000 | 100.0 | 100.0 | 100.0 | 0.067 |
| Ex. 4a | Sol-gel method | PrPO₄ | Monazite monoclinic | 600 | 100.0 | 100.0 | 100.0 | 0.31 |
| Ex. 4b | Sol-gel method | PrPO₄ | Monazite monoclinic | 800 | 100.0 | 100.0 | 100.0 | 0.18 |
| Ex. 5a | Sol-gel method | NdPO₄ | Monazite monoclinic | 600 | 100.0 | 100.0 | 100.0 | 0.34 |
| Ex. 5b | Sol-gel method | NdPO₄ | Monazite monoclinic | 1,000 | 100.0 | 100.0 | 100.0 | 0.15 |
| Comp. Ex. 1 | Coprecipitation method | YPO₄ | Xenotime tetragonal | 1,100 | 94.0 | 93.9 | 92.1 | — |
| Comp. Ex. 2a | Coprecipitation method | LaPO₄ | Monazite monoclinic | 900 | 99.8 | — | — | — |
| Comp. Ex. 2b | Coprecipitation method | LaPO₄ | Monazite monoclinic | 1,100 | 82.4 | — | — | — |
| Comp. Ex. 3a | Coprecipitation method | CePO₄ | Rabdophane hexagonal | 600 | 100.0 | 98.4 | 97.1 | 0.40 |
| Comp. Ex. 3b | Coprecipitation method | CePO₄ | Monazite monoclinic | 1,100 | 95.8 | 94.1 | 93.5 | 0.035 |
| Comp. Ex. 3c | Coprecipitation method | CePO₄ | Monazite monoclinic | 1,200 | 69.4 | 62.7 | 69.0 | 0.016 |

GLY: glycerin
Deposition amount: the amount of carbonaceous substance deposited per 1 g of each catalyst after 7 hours As shown in Table 2, Examples using the catalysts prepared by the sol-gel method exhibited as a whole higher GLY conversion rates than those in Comparative Examples using the catalysts prepared by the co-precipitation method.

The selectivities of acrolein (ACR), propionaldehyde (PALD), 1-hydroxyacetone (HDAC), and phenol (PhOH) are shown in Table 3 below.

TABLE 3

| | Catalysts | | | Calcination temperature (°C.) | GLY conversion rates (%) After 3 hours | | | |
|---|---|---|---|---|---|---|---|---|
| | Preparation method | Catalyst composition | Crystal structure | | ACR | PALD | HDAC | PhOH |
| Ex. 1a | Sol-gel method | YPO₄ YPO₄ | tetragonal Xenotime tetragonal | 600 | 56.8 | 2.6 | 18.2 | 0.7 |
| Ex. 1b | Sol-gel method | YPO₄ | Xenotime tetragonal | 1,100 | 66.1 | 1.9 | 9.7 | 0.5 |
| Ex. 2a | Sol-gel method | LaPO₄ | Monazite monoclinic | 600 | 57.5 | 2.7 | 5.8 | 0.4 |
| Ex. 2b | Sol-gel method | LaPO₄ | Monazite monoclinic | 800 | 55.8 | 2.5 | 3.5 | 0.4 |
| Ex. 3a | Sol-gel method | CePO₄ | Monazite monoclinic | 600 | 56.8 | 4.1 | 4.2 | 0.3 |
| Ex. 3b | Sol-gel method | CePO₄ | Monazite monoclinic | 1,000 | 68.6 | 1.7 | 7.8 | 0.4 |

TABLE 3-continued

| | | | | | | | | |
|---|---|---|---|---|---|---|---|---|
| Ex. 4a | Sol-gel method | PrPO$_4$ | Monazite monoclinic | 600 | 62.4 | 4.0 | 9.0 | 0.8 |
| Ex. 4b | Sol-gel method | PrPO$_4$ | Monazite monoclinic | 800 | 53.6 | 2.6 | 6.8 | 0.6 |
| Ex. 5a | Sol-gel method | NdPO$_4$ | Monazite monoclinic | 600 | 76.4 | 2.6 | 1.5 | 0.1 |
| Ex. 5b | Sol-gel method | NdPO$_4$ | Monazite monoclinic | 1,000 | 77.9 | 4.2 | 8.7 | 0.9 |
| Comp. Ex. 1 | Coprecipitation method | YPO$_4$ | Xenotime tetragonal | 1,100 | 32.2 | 2.3 | 19.8 | 0.5 |
| Comp. Ex. 2a | Coprecipitation method | LaPO$_4$ | Monazite monoclinic | 900 | 17.6 | 3.3 | 13.7 | 0.9 |
| Comp. Ex. 2b | Coprecipitation method | LaPO$_4$ | Monazite monoclinic | 1,100 | 21.2 | 1.3 | 17.0 | 0.2 |
| Comp. Ex. 3a | Coprecipitation method | CePO$_4$ | Rabdophane hexagonal | 600 | 26.7 | 3.9 | 12.8 | 0.0 |
| Comp. Ex. 3b | Coprecipitation method | CePO$_4$ | Monazite monoclinic | 1,100 | 30.5 | 3.9 | 12.8 | 0.0 |
| Comp. Ex. 3c | Coprecipitation method | CePO$_4$ | Monazite monoclinic | 1,200 | 37.0 | 1.4 | 18.8 | 0.2 |

| | GLY conversion rates (%) | | | | | | | |
|---|---|---|---|---|---|---|---|---|
| | After 5 hours | | | | After 7 hours | | | |
| | ACR | PALD | HDAC | PhOH | ACR | PALD | HDAC | PhOH |
| Ex. 1a | 63.3 | 3.0 | 21.4 | 0.6 | 61.0 | 3.0 | 21.5 | 0.5 |
| Ex. 1b | 66.2 | 2.3 | 10.8 | 0.5 | 66.3 | 2.3 | 10.7 | 0.4 |
| Ex. 2a | 57.9 | 2.9 | 6.7 | 0.6 | 57.0 | 3.2 | 6.9 | 0.6 |
| Ex. 2b | 55.4 | 2.7 | 5.4 | 0.3 | 58.6 | 3.1 | 6.4 | 0.3 |
| Ex. 3a | 51.7 | 3.3 | 5.6 | 0.2 | 47.4 | 2.9 | 6.0 | 0.2 |
| Ex. 3b | 61.4 | 1.7 | 7.3 | 0.3 | 60.3 | 1.7 | 7.6 | 0.3 |
| Ex. 4a | 64.3 | 3.9 | 10.2 | 0.9 | 63.6 | 4.1 | 7.6 | 0.9 |
| Ex. 4b | 60.1 | 3.1 | 8.3 | 0.7 | 62.2 | 3.4 | 9.2 | 0.7 |
| Ex. 5a | 69.2 | 3.9 | 10.7 | 0.6 | 68.1 | 3.8 | 13.1 | 0.7 |
| Ex. 5b | 78.4 | 4.7 | 10.3 | 0.9 | 79.2 | 4.5 | 10.9 | 0.8 |
| Comp. Ex. 1 | 34.9 | 2.6 | 20.8 | 0.4 | 34.2 | 2.5 | 20.9 | 0.4 |
| Comp. Ex. 2a | — | — | — | — | — | — | — | — |
| Comp. Ex. 2b | — | — | — | — | — | — | — | — |
| Comp. Ex. 3a | 28.1 | 3.6 | 15.0 | 0.8 | 27.4 | 3.2 | 15.5 | 0.1 |
| Comp. Ex. 3b | 32.1 | 3.6 | 15.0 | 0.8 | 31.4 | 3.2 | 15.5 | 0.1 |
| Comp. Ex. 3c | 44.3 | 1.7 | 20.9 | 0.2 | 35.8 | 1.4 | 19.4 | 0.2 |

ACR: acrolein;
PALD: propionaldehyde;
HDAC: 1-hydroxyacetone;
PhOH: phenol

The selectivity of acrolein (ACR) and the yield of acrolein (ACR yield) are shown in Table 4 below.

TABLE 4

| | Catalysts | | | Calcination temperature (° C.) | ACR conversions (%) | | | ACR yields (%) | | |
|---|---|---|---|---|---|---|---|---|---|---|
| | Preparation method | Catalyst composition | Crystal structure | | After 3 hours | After 5 hours | After 7 hours | After 3 hours | After 5 hours | After 7 hours |
| Ex. 1a | Sol-gel method | YPO$_4$ YPO$_4$ | tetragonal Xenotime tetragonal | 600 | 56.8 | 63.3 | 61.0 | 56.8 | 63.3 | 61.0 |
| Ex. 1b | Sol-gel method | YPO$_4$ | Xenotime tetragonal | 1,100 | 66.1 | 66.2 | 66.3 | 66.1 | 66.2 | 66.3 |
| Ex. 2a | Sol-gel method | LaPO$_4$ | Monazite monoclinic | 600 | 57.5 | 57.9 | 57.0 | 57.5 | 57.9 | 57.0 |
| Ex. 2b | Sol-gel method | LaPO$_4$ | Monazite monoclinic | 800 | 55.8 | 55.4 | 58.6 | 55.8 | 55.4 | 58.6 |

TABLE 4-continued

| | | Catalysts | | Calcination | ACR conversions (%) | | | ACR yields (%) | | |
|---|---|---|---|---|---|---|---|---|---|---|
| | Preparation method | Catalyst composition | Crystal structure | temperature (° C.) | After 3 hours | After 5 hours | After 7 hours | After 3 hours | After 5 hours | After 7 hours |
| Ex. 3a | Sol-gel method | $CePO_4$ | Monazite monoclinic | 600 | 56.8 | 51.7 | 47.4 | 56.8 | 51.7 | 47.4 |
| Ex. 3b | Sol-gel method | $CePO_4$ | Monazite monoclinic | 1,000 | 68.6 | 61.4 | 60.3 | 68.6 | 61.4 | 60.3 |
| Ex. 4a | Sol-gel method | $PrPO_4$ | Monazite monoclinic | 600 | 62.4 | 64.3 | 63.6 | 62.4 | 64.3 | 63.6 |
| Ex. 4b | Sol-gel method | $PrPO_4$ | Monazite monoclinic | 800 | 53.6 | 60.1 | 62.2 | 53.6 | 60.1 | 62.2 |
| Ex. 5a | Sol-gel method | $NdPO_4$ | Monazite monoclinic | 600 | 76.4 | 69.2 | 68.1 | 76.4 | 69.2 | 68.1 |
| Ex. 5b | Sol-gel method | $NdPO_4$ | Monazite monoclinic | 1,000 | 77.9 | 78.4 | 79.2 | 77.9 | 78.4 | 79.2 |
| Comp. Ex. 1 | Coprecipitation method | $YPO_4$ | Xenotime tetragonal | 1,100 | 32.2 | 34.9 | 34.2 | 30.1 | 32.8 | 31.5 |
| Comp. Ex. 2a | Coprecipitation method | $LaPO_4$ | Monazite monoclinic | 900 | 17.6 | — | — | 17.5 | — | — |
| Comp. Ex. 2b | Coprecipitation method | $LaPO_4$ | Monazite monoclinic | 1,100 | 21.2 | — | — | 17.5 | — | — |
| Comp. Ex. 3a | Coprecipitation method | $CePO_4$ | Rabdophane hexagonal | 600 | 26.7 | 28.1 | 27.4 | 26.7 | 27.6 | 26.6 |
| Comp. Ex. 3b | Coprecipitation method | $CePO_4$ | Monazite monoclinic | 1,100 | 30.5 | 32.1 | 31.4 | 29.2 | 30.2 | 29.4 |
| Comp. Ex. 3c | Coprecipitation method | $CePO_4$ | Monazite monoclinic | 1,200 | 37.0 | 44.3 | 35.8 | 25.7 | 27.7 | 24.7 |

ACR: acrolein

In Table 4, the selectivities and yields in Examples employing the sol-gel method can be confirmed to have been higher than those in Comparative Examples employing the co-precipitation method. Further, in comparison among Examples, the selectivities and yields in Examples 5a and 5b using Nd as a rare earth metal can be confirmed to have been high.

The invention claimed is:

1. A process for producing acrolein by dehydration of glycerin in a presence of a catalyst, wherein the catalyst comprises a rare earth metal salt crystal of phosphoric acid and the crystal is obtained by calcining a solid which is formed by allowing a liquid containing water and a hydroxide of the rare earth metal and/or a dehydration condensate of the hydroxide to contain phosphate ions.

2. The process for producing acrolein according to claim 1, wherein the glycerin is dehydrated by gas-phase dehydration in which glycerin gas is brought into contact with the catalyst.

3. The process for producing acrolein according to claim 1, wherein the hydroxide of the rare earth metal and/or the dehydration condensate of the hydroxide are produced by mixing an alkaline compound in an aqueous solution of a water-soluble rare earth metal salt.

4. The process for producing acrolein according to claim 3, wherein the water-soluble rare earth metal salt is one kind or two or more kinds of salts selected from nitrates, carbonates, chlorides, and organic acid salts.

5. The process for producing acrolein according to claim 1, wherein the rare earth metal of the crystal is one kind or two or more kinds of rare earth metals selected from Y, La, Ce, Pr, and Nd.

6. A process for producing an acrolein derivative, comprising steps of using the process for producing acrolein according to claim 1.

7. The process for producing an acrolein derivative according to claim 6, wherein the acrolein derivative is a water-absorbent resin.

* * * * *